US012768835B2

(12) United States Patent
Neilson et al.

(10) Patent No.: US 12,768,835 B2
(45) Date of Patent: Oct. 20, 2026

(54) METHOD AND APPARATUS FOR MEASURING PHYSIOLOGICAL PROPERTIES OF BIOLOGICAL SAMPLES

(71) Applicant: Agilent Technologies, Inc., Santa Clara, CA (US)

(72) Inventors: Andrew C Neilson, Sunapee, NH (US); Paul D McGarr, Longmeadow, MA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 18/126,809

(22) Filed: Mar. 27, 2023

(65) Prior Publication Data

US 2023/0228743 A1 Jul. 20, 2023

Related U.S. Application Data

(63) Continuation of application No. 15/480,586, filed on Apr. 6, 2017, now Pat. No. 11,639,925.

(51) Int. Cl.

| | |
|---|---|
| ***G01N 33/53*** | (2006.01) |
| ***B01L 3/00*** | (2006.01) |
| ***C12M 1/34*** | (2006.01) |
| ***G01N 21/03*** | (2006.01) |
| ***G01N 21/64*** | (2006.01) |

(52) U.S. Cl.

CPC ...... *G01N 33/5302* (2013.01); *B01L 3/50853* (2013.01); *C12M 41/46* (2013.01); *G01N 21/03* (2013.01); *G01N 21/6452* (2013.01); *G01N 33/5304* (2013.01); *B01L 2300/0609* (2013.01); *B01L 2300/0627* (2013.01); *B01L 2300/0829* (2013.01); *G01N 2021/0325* (2013.01)

(58) Field of Classification Search

None

See application file for complete search history.

(56) References Cited

U.S. PATENT DOCUMENTS

| | | | |
|---|---|---|---|
| 4,225,575 | A | 9/1980 | Piasio et al. |
| 4,483,925 | A | 11/1984 | Noack |
| 4,889,816 | A | 12/1989 | Davis et al. |
| 5,217,875 | A | 6/1993 | Karpf et al. |
| 5,225,164 | A | 7/1993 | Astle |
| 5,496,697 | A | 3/1996 | Parce et al. |
| 5,718,842 | A | 2/1998 | Papkovsky et al. |
| 6,395,506 | B1 | 5/2002 | Pitner et al. |
| 6,730,471 | B1 | 5/2004 | Katerkamp et al. |
| 7,276,351 | B2 | 10/2007 | Teich et al. |

(Continued)

FOREIGN PATENT DOCUMENTS

| | | | |
|---|---|---|---|
| CN | 101506643 | A | 8/2009 |
| CN | 104471052 | A | 3/2015 |

(Continued)

OTHER PUBLICATIONS

EPO, "Extended European Search Report Mailed on Mar. 21, 2018," Application No. 18150147.9, 9 pages.

(Continued)

*Primary Examiner* — William H. Beisner

(57) ABSTRACT

The present disclosure relates to methods and apparatus for measuring of multiple physiological properties of biological samples, such as measuring biological flux.

19 Claims, 2 Drawing Sheets

(56) References Cited

U.S. PATENT DOCUMENTS

| | | | | |
|---|---|---|---|---|
| 8,202,702 | B2 | 6/2012 | Neilson et al. | |
| 11,639,925 | B2 * | 5/2023 | Neilson | G01N 21/6452 435/287.9 |
| 2002/0100582 | A1 | 8/2002 | Oldenburg | |
| 2003/0124029 | A1 | 7/2003 | Webb et al. | |
| 2004/0152210 | A1 | 8/2004 | Joos et al. | |
| 2005/0054028 | A1 | 3/2005 | Teich et al. | |
| 2005/0239197 | A1 | 10/2005 | Katerkamp et al. | |
| 2007/0087401 | A1 | 4/2007 | Neilson et al. | |
| 2010/0124761 | A1 | 5/2010 | Neilson et al. | |
| 2018/0008944 | A1 | 1/2018 | Ozeki | |

FOREIGN PATENT DOCUMENTS

| | | | | |
|---|---|---|---|---|
| DE | 202004020847 | U1 * | 3/2006 | B01L 3/50853 |
| EP | 2920292 | A2 | 9/2015 | |
| JP | H04500307 | A | 1/1992 | |
| JP | 2001521162 | A | 11/2001 | |
| JP | 2002533727 | A | 10/2002 | |
| JP | 2005516596 | A | 6/2005 | |
| JP | 2005528582 | A | 9/2005 | |
| JP | 2007505316 | A | 3/2007 | |
| JP | 2016503299 | A | 2/2016 | |
| WO | 02072423 | A1 | 9/2002 | |
| WO | 2014198836 | A1 | 12/2014 | |

OTHER PUBLICATIONS

Mitoxpress, et al., "Intracellular Product Specifications," PI-03, Ver 03/13, Mar. 2013.

Presens, et al., "PreSens GmbH (OxoPlate OP96U)," Downloaded from PreSens website, Apr. 5, 2017.

Presens, et al., "PreSens OxoPlate OP96U," Manual, Mar. 1, 2004.

Translation of Chinese Office Action for Application No. 202310001455.4, dated Jun. 18, 2025, 13 pages.

* cited by examiner

METHOD AND APPARATUS FOR MEASURING PHYSIOLOGICAL PROPERTIES OF BIOLOGICAL SAMPLES

CROSS-REFERENCE TO RELATED APPLICATIONS

This application is a continuation of U.S. patent application Ser. No. 15/480,586, filed on Apr. 6, 2017, the contents of which are fully incorporated herein by reference.

FIELD OF THE INVENTION

This disclosure relates to methods and apparatus for measuring of multiple physiological properties of biological samples, such as measuring biological flux.

BACKGROUND

Living cells typically consume oxygen (O2) from their surrounding environment and release metabolic byproducts, such as carbon dioxide (CO2), lactate, and various other metabolic byproducts. Flux analyzers allow one to measure the oxygen consumption rate (OCR), extracellular acidification rate (ECAR), CO2 production rate (CPR), and/or other biological flux parameters. Such measurements can provide valuable information regarding the metabolic processes carried out by these living cells.

One known method of measuring the OCR and ECAR of living cells is by measuring flux of O2 and H+ generated by these living cells in a wellplate using a set of fluorescent sensors. An example of an analyzer using fluorescent sensors to detect flux of O2 and H+ is the Seahorse flux analyzer, which is generally described in U.S. Pat. Nos. 7,276,351 and 8,202,702. The fluorescent sensors measure the intensity of fluorescent signals over time. For a sample containing living cells, those signals over time will be proportional to the rate of production or consumption of O2 molecules and H+ ions consumed or produced by the metabolism of the cells. This data is used to calculate the flux of O2 molecules and H+ ions consumed and produced by the living cells.

Problems connected with flux analyzers and flux measurements include a difficulty in using and manufacturing such devices, and in obtaining the desired levels of precision and accuracy.

PreSens GmbH of Regensburg, Germany manufactures a sensor plate (OxoPlate OP96U) which uses a fluorescent dye embedded in a hydrogel substrate deposited in the bottom of a conventional 96-well well plate. The product is designed to work with a detection system which measures the decay time of the fluorescent dye by applying an oscillatory input (excitation) and reading the phase shift of the primary reactive dye to a reference dye. The biological sample is placed within the well, on top of the dye, and allowed to equilibrate over a period of time in which the entire well comes to equilibrium with the analyte being measured. Drawbacks include long equilibration time due to the large open volume; non-standard plates containing fluorescent dye; the sensor in the bottom of the plate may affect cell growth/proliferation; limited to single analyte; and proprietary electro-optics.

U.S. Pat. No. 6,395,506 (Becton Dickerson) discloses a luminescence detection system which makes use of the sensitivity of the luminescent emission of certain compounds to the presence of oxygen, which quenches (diminishes) the compound's luminescent emission in a concentration dependent manner. Becton Dickerson also produced a product called OBS Bioplate which was discontinued. The BD plates were capable of being read in a generic plate reader by measuring the ratiometric intensity of a single excitation dual emission luminescent dye that was quenched in the presence of oxygen. In this configuration the fluorescent dye was deposited in the bottom of the plate and had similar disadvantages as the PreSens product.

U.S. Pat. No. 5,718,842 (Joanneum Reserach) discusses a luminescent dye including a metallocomplex of an oxoporphyrin. Luxcel manufactures a phosphorescent oxygen probe kit which contains a luminescent dye which is dissolved into the medium along with the biological sample. The kits can be read in a standard plate reader, are scalable for high throughput but lack sensitivity. Another drawback is contamination of the sample, as the sensor is dissolved in the medium. Other drawbacks are long equilibration time due to the large open volume, though this may be shortened by adding an oil layer on top of the media; and invasiveness, since the luminescent probe is dissolved in the medium.

Pall ForteBio LLC of Fremont, Calif. manufactures a dip and read assay based on a sandwiched ELISA (enzyme-linked immunosorbent assay) for measuring proteins. The biosensor assays are coated with a matrix protein on the distal end of a sensor probe. The sensors react to binding of the protein by changing the interference pattern as read by the instrument. The drawback to this system are limited kits for kinetic binding, and single end point readout (of a specific binding event).

U.S. Pat. No. 5,496,697 (Molecular Devices Corp.) discusses methods and apparatus for detecting the effects of cell affecting agents on living cells. Living cells are retained in a micro flow chamber. The micro flow chamber is adapted for either continuous or intermittent flow of solutions or suspensions in intimate contact with the cells. The solutions or suspensions, which contain a cell affecting agent, are then flowed in intimate contact with the cells and the pit is measured.

Molecular Devices Corp. of Sunnyvale, Calif. previously sold a product named "Cytosensor" for measuring changes in pH within a small enclosed chamber using a light addressable potentiometric sensor. The product has been discontinued. The product was based on a perfusion system which periodically stopped the flow of the medium through the chamber. During the stop flow period, a small chamber was created, amplifying flux and measurements of pH were taken over multiple time points. Potential drawbacks to this system include its complex perfusion system; limited to single analyte (pH); non-standard plates; it was difficult to scale (sold in 8 well format); and proprietary electro-optics.

There remains a need for apparatus and methods that are adaptable and easy to manufacture and use for the measurement of biological analytes.

SUMMARY

The present disclosure provides apparatus and methods for measuring physiological properties of one or more analytes consumed and/or produced by a biological system or biological sample disposed in media.

DETAILED DESCRIPTION OF EMBODIMENTS

Figure 1:
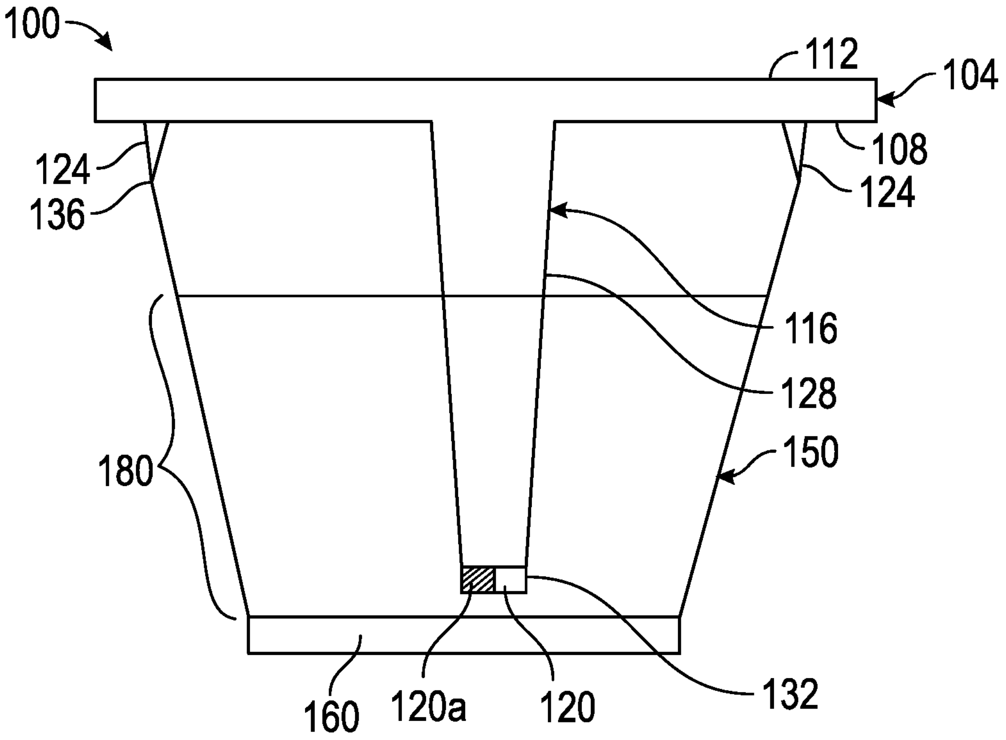
FIG. 1 is a front cross-sectional view of one embodiment of an apparatus of the present disclosure showing the spine of the apparatus disposed in a well of a well plate containing a biological sample surrounded by media.

The term "flux" as used herein means change of a parameter as a function of time. The change may be expected due to consumption or reaction of a reactant represented by the parameter.

As one aspect, the present disclosure provides an apparatus for measuring one or more physiological properties of a biological sample. The apparatus comprises a lid having a first surface and a second surface; a plurality of spines connected to and extending from the first surface of the lid, each of the plurality of spines comprising a body having a distal end; and a sensor disposed on the distal end of the at least one of the plurality of spines, wherein the sensor is to engage and provide a signal responsive to one or more analytes.

As another aspect, the present disclosure provides a system for measuring one or more physiological properties of a biological sample. The system comprises a well plate having a plurality of wells. The wells having an open end and a closed end opposite the open end. The system can also include any of the apparatus comprising a lid and a plurality of spines which disclosed herein. The plurality of spines extends into the wells through the open end. The system can also include a signal detector in a position to detect a signal from the sensor, for example a plate reader or a charge coupled device (CCD) camera. The system can also include a processor in communication with the signal detector.

As yet another aspect, the present disclosure provides a method for manufacturing an apparatus for measuring one or more physiological properties of a biological sample. The method can be used to manufacture any of the apparatus comprising a lid and a plurality of spines which disclosed herein. For example, the method can comprise providing a lid having a first surface and a second surface and a plurality of spines connected to and extending from the first surface of the lid. Each of the plurality of spines comprising a body having a distal end. The method also comprises applying a sensor to the distal end of at least one of the plurality of spines, wherein the sensor is to engage and provide a signal responsive to one or more analytes. In some embodiments, the lid is provided by molding a polymer material to form the lid and the plurality of spines.

In use, certain embodiments of the apparatus of the present disclosure engage a well plate that defines wells. Each well includes a biological sample disposed in media. The spines of the apparatus are inserted or disposed into the wells such that the sensor disposed on the distal end of each spine can engage one or more analytes consumed and/or produced by the biological sample in the media. The sensor produces a signal responsive to one or more analytes, and the signal may indicate the amount or concentration of such analytes. Various known methods are performed to detect a signal from the sensor, such as by detecting an optical signature, to measure a change of concentration of the one or more analytes at various time points. These measurements can further be used to compute the flux as a function of time of the one or more analytes.

Referring now to FIG. 1, one embodiment of the apparatus of the present disclosure is shown. In various embodiments, the apparatus 100 includes: (1) a lid 104 having a first surface 108 and a second surface 112; (2) spines 116 connected to and extending from the first surface 108; (3) at least two sensors 120, **120*a* disposed on each spine 116; and (4) protrusions 124 connected to and extending from the first surface 108**.

In some embodiments, the apparatus includes one or more spines. It should be appreciated that each of the spines in certain embodiments is identical or substantially identical. Therefore, the spine 116 shown in FIG. 1 and discussed in further detail below is an example of the spines included in certain embodiments. However, it should be appreciated that the spines do not need to be identical or substantially identical and can vary based on the respective positions and connections to or formations with the other members of the apparatus of the present disclosure. In some embodiments, the plurality of spines comprises 24 spines, alternatively 48 spines, alternatively 96 spines, alternatively 384 spines, alternatively 1536 spines, so that it corresponds or cooperates with a standardized well plate.

As best shown in FIG. 1, the spine 116 includes a radially tapered body 128 having a distal end 132. In this embodiment, the distal end 132 of the body 128 has a diameter of about 1 millimeter. In other embodiments, the distal end 132 can have a diameter that is greater than 1 millimeter or less than 1 millimeter.

In some embodiments, each of the plurality of spines 116 has a length, and the length is between 1 mm and 20 mm, alternatively between 5 mm and 15 mm, alternatively about 10 mm. In some embodiments, the plurality of spines collectively has a mean length, and the length of each of the plurality of spines is within 20% of the mean length, alternatively within 10%, alternatively within 5%. In some embodiments, distal end has a substantially flat surface, and/or the surface area of the distal end of the spine is between 0.01 $mm^2$ and 16 $mm^2$, alternatively between 0.25 $mm^2$ and 4 $mm^2$ , alternatively about 1 $mm^2$. though should further be appreciated that the surface area can be another suitable size that is greater than 16 $mm^2$ or less than 0.01 $mm^2$. In some embodiments, the distal end of the spine 116 is substantially circular, with a diameter between 0.1 mm and 2 mm, alternatively between 0.5 mm and 1.5 mm, alternatively about 1 mm. Additionally, the spine 116 can be positioned equidistantly or substantially equidistantly from another spine(s) when connected to and extending from the first surface 108 of the lid 104. For example, in certain embodiments, the spine 116 is positioned between 1 and 20 mm, alternatively about 10 mm, from another spine(s) 116. It should further be appreciated that the distance between two or more spines can be another suitable length that is greater 10 mm or less than 10 mm.

In some embodiments, the distal end of each of the plurality of spines extends through an open end of a well, toward a closed end opposite the open end. The distal end can be at a distance from the closed end, for example between 50 micrometers and 800 micrometers from the closed end of the well, alternatively between 100 micrometers and 400 micrometers, alternatively about 200 micrometers.

Certain embodiments can include spine(s) that are removably connected to the lid. For example, the proximal end of the spine(s) may have threads that are reciprocal to threads in the lid. Alternatively, the proximate end may be sized, or have have a portion configured, for a compression fit in a hold in the lid. It should be appreciated that alternative embodiments can include spine(s) that are integrally connected to the lid.

In some embodiments, the apparatus includes spines having a sensor on each of the spines. More specifically, in certain embodiments the sensor 120 is disposed on the distal end 132 of the body 128 of the spine 116. The sensor 120 is configured to engage one or more analytes and provide a signal to be detected by a suitable measurement device, as further discussed below. In certain embodiments, all spines need not have a sensor disposed on each spine. Additionally, it should be appreciated that the sensor can be disposed on another suitable portion of the body of the spine other than the distal end.

In some embodiments, the apparatus has a plurality of spines attached to a lid, and each spine has a substantially identical sensor. For example, each spine has the same fluorophore(s) in substantially identical amounts and spread evenly over the flat distal end of the spine. In some embodiments, the apparatus has a plurality of spines attached to a lid, and at least two of the spines have a different amount of a sensor. For example, a first spine of the plurality of spines can have a first amount of the sensor, and a second spine of the plurality of spines can have a second amount of the sensor; the apparatus may also comprise spines having a third, fourth, and additional amounts of the sensor. In some embodiments, the apparatus has a plurality of spines attached to a lid, and at least two of the spines have different sensors. For example, one or more of the plurality of the spines can have a first sensor, and one or more of the plurality of the spines can have a second sensor. The apparatus may also comprise spines having a third, fourth, and additional types of sensors.

In some embodiments, each spine has an amount of sensor that differs less than 20%, alternatively less than 10%, alternatively less than 5%, from a near amount of sensor on all the plurality of spines of the lid.

In some embodiments, the sensor is an indicator embedded in a permeable medium, such as an oxygen permeable medium. For example, the sensor can be a fluorescent indicator, such as an oxygen-quenched fluorophore, embedded in an oxygen permeable medium, such as a hydrogel. In some embodiments, the fluorescent indicator is selected from HPTS, fluorescein, porphyrin, and ruthenium. The fluorescent indicator provides a fluorescent signal which is dependent on the presence and/ or concentration of a constituent in the well. Other types of known sensors may be used, such as electrochemical sensors, ISFET (ion-sensitive field-effect transistor) sensors, amperametric sensors such as the Clark electrode, biologically sensitive elements such as antibodies and nucleic acids, for example. In other embodiments, the sensor can be another suitable sensor that is configured to be detected by a suitable measurement device.

In some embodiments, the indicator is embedded in a permeable medium, such as a permeable medium selected from hydrogel, silicone, and matrigel. In some embodiments, the sensor is attached to the plurality of spines by solidifying or removing the medium (such as by drying, curing, cooling, evaporating or other technique). The sensor can applied by dipping or spotting the distal end of at least one of the plurality of spines in a mixture of a fluorescent indicator in a medium.

It should be appreciated that in certain embodiments, the sensor can be spotted or dipped onto the body of the spine of the apparatus. It should further be appreciated that in certain embodiments, the sensor can be removably connectable to the body of the spine of the apparatus. It should further be appreciated that in certain embodiments, the sensors can be integrally formed with the body of the spine of the apparatus. Obtaining substantially identical sensors on a plurality of spines requires careful, specially designed manufacturing techniques, such as vapor deposition, chemical coating, spin coating, dipping, and robotic spotting.

In some embodiments, the lid also includes one or more spacing protrusions. The protrusions 124 can be any suitable shape, such as rounded, conical, or triangular shape. The protrusions 124 are configured to engage a surface of a well plate such that the first surface 108 of the lid 104 does not engage said surface of the well plate. More specifically, as shown in FIG. 1, the protrusions 124 engage the surface 136 of the well plate 150 such that a distance or space exists between the surface 136 of the well plate 150 and the first surface 108 of the lid 104. In certain embodiments, this distance can vary depending on the length of the protrusions 124. It should be appreciated that the protrusions can be another suitable shape. It should further be appreciated that in alternative embodiments, the apparatus of the present disclosure does not have to include protrusions. In such alternative embodiments, the apparatus can include another suitable member that forms a distance between the first surface 108 of the lid 104 and the surface 136 of the well plate 150. In some embodiments, the protrusions 124 are reciprocal to indents on the well plate 150, and together they form an alignment mechanism that ensures or assists proper positioning of the lid on the well plate.

In certain embodiments, the apparatus 100 engages the well plate 150 such that each spine 116 is disposed in the well with which it aligns. The wells include a biological sample 160 disposed in media. The biological sample can be prokaryotic or eukaryotic cells, preferably eukaryotic cells, which consume oxygen gas or another suitable metabolic compound(s).

Within the well in the area of the sample, a gradient of analytes is formed. This gradient 180 is generally formed when the biological sample 160 consumes and/or produces the one or more analytes (not shown) that engage the sensor 120.

In use, the spines are disposed in the wells to a pre-determined depth. As shown in FIG. 1, the sensor 120 and/or the spine 116 does not engage the biological sample 160. In certain embodiments, this pre-determined depth is 50 to 800 micrometers, alternatively 100 to 400 micrometers, alternatively 200 micrometers above the biological sample. In some, embodiments, this pre-determined depth is greater than, or less than, 200 micrometers. In some embodiments, this pre-determined depth can be altered by changing the length of the spine, the size of the sensor, the dimensions of the well plate, or a combination thereof. When disposed in the wells to a pre-determined depth, the spines can define a sub-chamber, wherein the sub-chamber can be defined as the space between the proximal end of the sensor and a mono-layer of cells of the biological sample. The size of the sub-chamber can vary, such as when one or more properties of the spine, another member of the apparatus, and/or the biological sample is altered. The formation of the sub-chamber can allow the sensor to measure the biological flux of one or more analytes with high sensitivity and reproducibility over multiple measurements of the biological sample.

Upon disposing the spines 116 into the wells, the sensor 120 engages the one or more analytes consumed and/or produced by the biological sample 160 in the gradient 180. The concentration of the one or more analytes in the gradient 180 changes over time. The sensor(s) detect the change by providing increased or decreased signal. To measure this change in concentration of the one or more analytes in the gradient 180, the sensor 120 provides a signal detected by a signal detector such as plate reader or a non-scanning image based acquisition system, for example a CCD based camera or sensor chip. A device used to detect a signal from the sensor 120 is connected to a processor(s) by a suitable means. In such case, interrogation of the sensor 120 results in the processor(s) analyzing data collected by the sensor 120 by computing the change in concentration in the gradient at various time points of the one or more analytes. These measurements can further be analyzed to compute the flux of the one or more analytes as a function of time. Measurements can be collected until the one or more analytes comes to a steady state equilibrium. At such point, there is no substantial change of the concentration of the one or more analytes in the gradient 180; therefore, computation of the flux as a function of time of the one or more analytes is complete.

Figure 3:
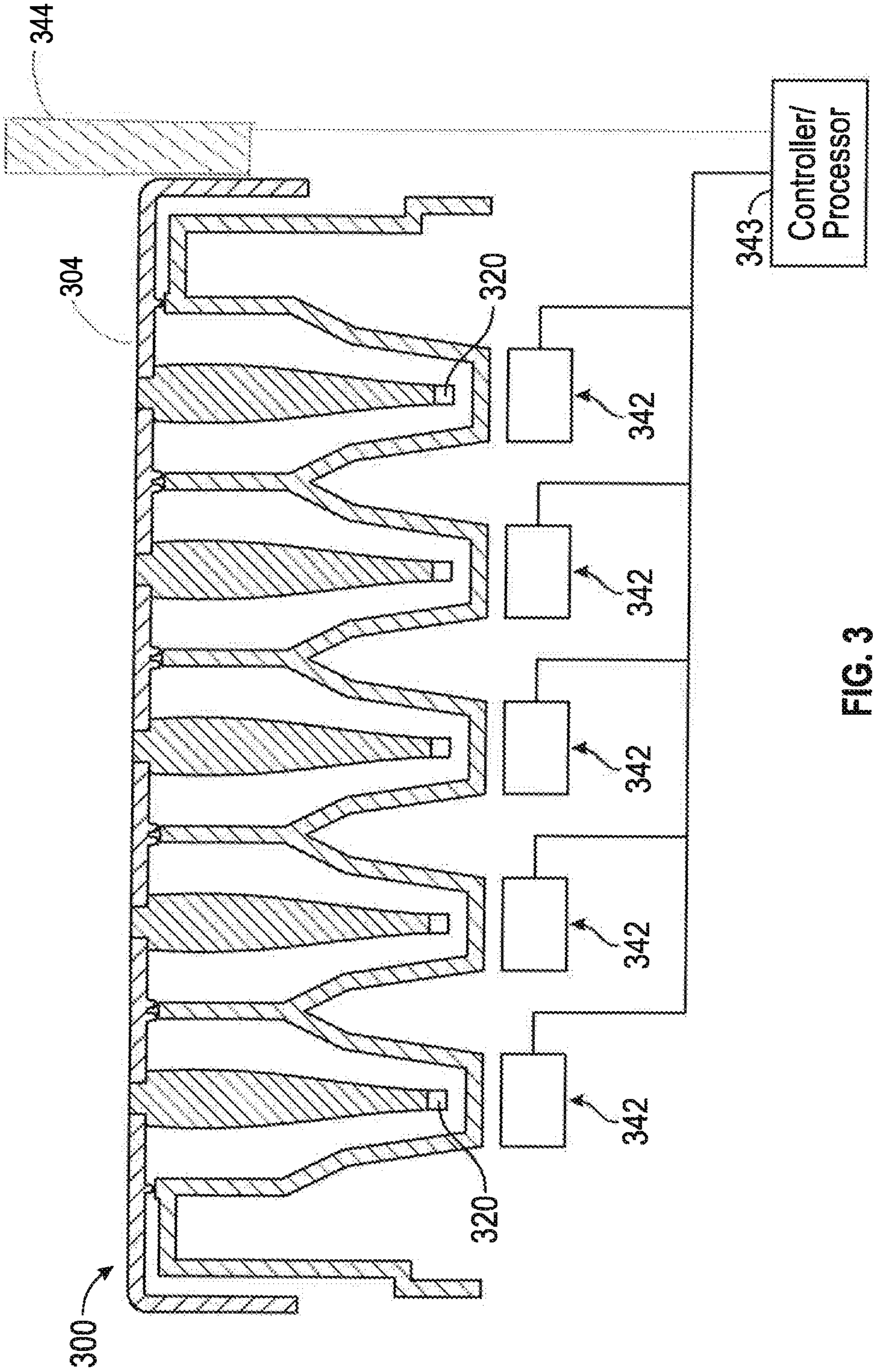
FIG. 3 is an illustration of an embodiment of the apparatus that comprises a signal detector and a processor.

An exemplary embodiment of an apparatus comprising a signal detector is shown in FIG. 3. The signal detector is a CCD based camera 342 interrogating the sensor 320. The camera 342 is positioned relatively underneath the sensor 320 and the bottom of the well so that the camera 342 can detect a signal from the sensor 320. The camera 342 is electrically connected to a controller/processor 343 which is configured to perform computations to analyze data sensed by the sensor 320 and collected by the camera 342.

Figure 2:
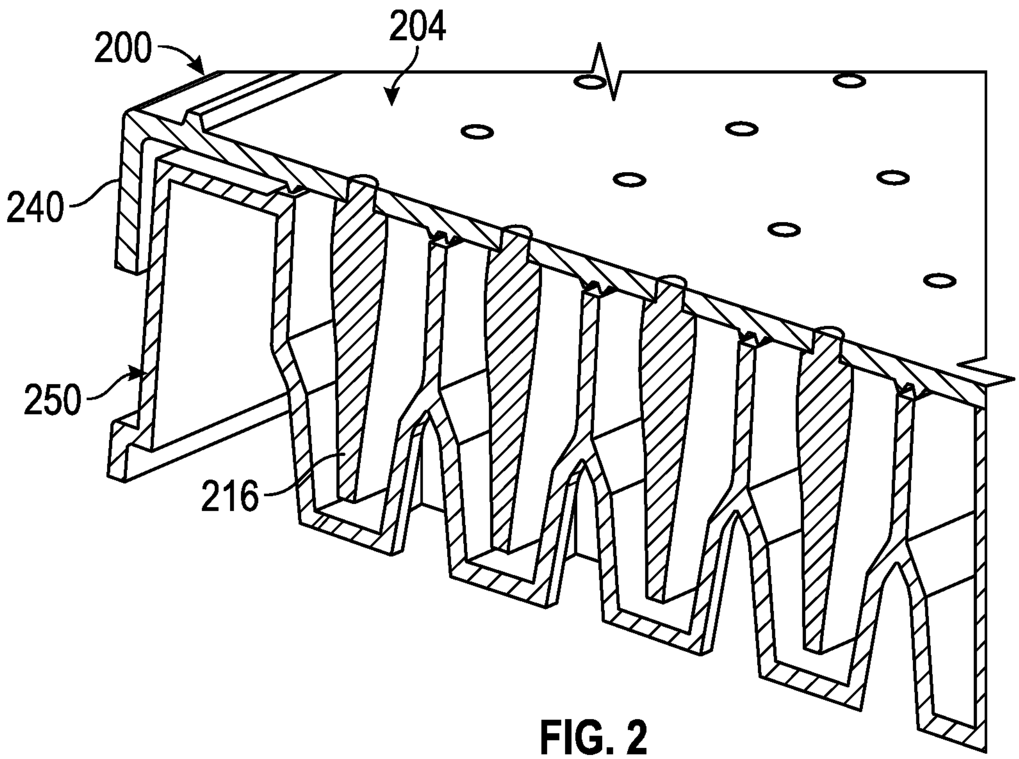
FIG. 2 is a perspective view of one embodiment of the apparatus of the present disclosure engaging a well plate.

The apparatus of the present disclosure can be well-configured to be used with a standard well plate, such as a 24-well well plate, 48-well well plate, 96-well well plate, 384-well well plate, or 1536-well well plate. The well plate may conform to an SBS (Society for Biomolecular Screening) standard. In such case, some embodiments can include a number of spines equal to or less than the number of wells defined by the well plate with which the apparatus engages. For example, if the apparatus is configured to engage a standard 96-well plate, then the apparatus can include ninety-six or less than ninety-six spines. In alternative embodiments and as shown in FIG. 2, the apparatus 200 can be configured to conform to a suitable Seahorse well plate 250, such as the well plate used in the Seahorse XF measurement system. Further detail on the use of the well plate is provided in U.S. Pat. No. 7,276,351, incorporated by reference herein. In such certain embodiments, the apparatus 200 can include a number of spines 216 equal to, greater than, or less than the number of wells defined by the well plate 250. For example, for a well plate 250 having 24 wells, an apparatus may comprise 12, 24 or 48 spines (or another number). An apparatus may comprise 1, 2, 3, 4, or more spines configured or arranged for insertion into a single well of a well plate. may As shown in FIG. 2, the spines 216 are disposed in the wells of the well plate 250 to a pre-determined depth so that, in use, the sensors on the spines 216 can engage the one or more analytes consumed and/or produced by the biological sample in the gradient in the wells.

It should be appreciated that in use the apparatus of the present disclosure can be moved; or the well plate can be moved to dispose the spines of the apparatus into the wells of the well plate, or both.

In some embodiments, the apparatus of the present disclosure can include a first lip 240 (as shown in FIG. 2); a second lip (not shown); a third lip (not shown); and a fourth lip (not shown). Each lip can be integrally connected to and extend perpendicularly from the lid 204. Each lip is configured to engage a side of the well plate so that the lid does not substantially move when the spines 216 are disposed in the wells of the well plate.

It should be appreciated that another suitable measurement device other than a plate reader or a CCD based camera can be used to detect a signal from the sensors. The measurement device can have one or more detection modes, such as detection of absorbance, fluorescence intensity, luminescence, time-resolved fluorescence, and/or fluorescence polarization. Plate readers having those detection modes are commercially available. In some embodiments, the sensors can be viewed from a position opposite a closed end of a well plate from the sensors. In some embodiments, the sensors can be interrogated from above the sensors, such as from above the lid of the apparatus; in such arrangements, a signal should be able to pass through the lid and/or spines so that it can be detected, for example, by having the lid and/or spines comprise a transparent material or translucent material, or having one or more fiber optics passing through or contained within the lid and/or spines.

It should further be appreciated that given the configuration of the spines of, and particularly the surface area of the spines, the spines may be disposed in the gradient in the wells for extended periods of time without contaminating or altering the local environment of the biological sample, such as causing hypoxia or a change in the local pH.

In some embodiments, the one or more analytes measured can be oxygen gas, hydrogen ions, or other metabolic analytes consumed and/or produced by the biological sample.

In some embodiments, the present apparatus can be configured, or have a sensor that responds to such other molecules. For example, such alternative embodiments can be configured to measure the concentration of signaling molecules including: insulin, glucagon, inflammatory markers (such as IL-7), or stimulator hormones (such as HIF). In such alternative embodiments, the sensor on the body of the spines can be an immobilized antibody. The apparatus can be transferred to various reservoirs to perform binding and washing steps so that the concentration of the one or more analytes of interest can be further measured. Since binding and washing occurs on the body of the spines of the apparatus instead of in wells of a well plate, the washing and binding steps can occur by moving the apparatus to different reservoirs instead of washing and adding reagents to wells of a well plate. To perform such steps, the apparatus can be moved into the reservoir or the reservoir can be moved toward the apparatus such that the molecule(s) on the body of the spine engage the molecule(s) in the reservoir.

In some embodiments, the apparatus can be configured to perform an ELISA assay. In such case, the sensor comprises a capture reagent, such as an antibody or antigen-binding fragment thereof. The capture reagent is a reagent capable of binding and capturing a target molecule in a sample such that under suitable condition, the capture reagent-target molecule complex can be separated from the rest of the sample. Typically, the capture reagent is immobilized or immobilizable. The capture reagent can be immobilized on the spine(s), preferably on a distal end of the spine(s), such as by covalently or noncovalent binding the capture reagent to a surface of the spine(s). In an apparatus adapted for a sandwich immunoassay, the capture reagent can be an antibody or a mixture of different antibodies against one or more target antigens. The antibody can be one or more monoclonal antibodies, polyclonal antibodies, multispecific antibodies (e.g. bispecific antibodies). The capture reagent can be one or more antibody fragments so long as they exhibit the antigen-binding activity of the antibody.

In some embodiments, an impeller can be connected to and extend from the body of the spines of the apparatus. In such alternative embodiments, the impeller can be integrally connected to or removably connectable to the body of the spines. The impeller can be configured to vibrationally or acoustically mix or perfuse the media that is in contact with or surrounds the biological sample. For example, such an alternative embodiment of the apparatus of the present disclosure can be placed on a surface that can vibrate. When this surface vibrates with the apparatus on it, the media surrounding the biological sample vibrates or moves. In such case, the impeller on the body of the spines engages the media and mixes the media. In doing so, mixing can create a homogenous mixture. Upon stopping vibration, and therefore mixing of the media, a sub-chamber between the sensor on the body of the spine and a monolayer of cells of the biological sample forms. In this sub-chamber, mixing is halted, and the signal(s) from the sensors can be viewed or detected to measure the change in concentration of the one or more analytes consumed and/or produced by the biological sample in the media. An advantage of including an impeller on the body of the spine is that the media surrounding the biological sample can be homogenously mixed at various times so that each time the sensors are viewed, the environment in which the biological sample resides homogenous and substantially free of local effects from the sensor such as the release of protons.

In some embodiments, the apparatus of the present disclosure can include a handle 344 attached to the lid 304. The handle 344 can be configured to allow movement of the apparatus of the present disclosure from a first position to one or more second positions. The movement can be manual, automatic, or both. The handle 344 can be in communication with and/or controlled by a processor 343, such as when automated movement is provided.

In some embodiments, the spines and/or lid are can be formed from a polymeric material, such as polypropylene, polycarbonate, or other suitable material or polymer. The spines and/or lid can be formed from a metal. Also, the spines and/or lid can be disposable. Additionally, the apparatus can be formed by a molding polymer material.

In some embodiments, the lid and/or spine can be solid. Additionally, may not be connected to any other device.

All of the references cited herein, including patents, patent applications, and publications, are hereby incorporated in their entireties by reference.

In the present disclosure, wherever the word "comprising" is found, it is contemplated that the words "consisting essentially of" or "consisting of" may be used in its place. Use of the singular includes the plural except where specifically indicated. Whenever the term "about" appears before a value, it should be understood that the specification is also providing a description of that value apart from the term "about", and vice versa.

In the present disclosure, any of the functions recited herein may be performed by one or more means for performing such functions. With respect to the processes described in the specification, it is intended that the specification also provides a description of the apparatus for performing those processes. With respect to the apparatus described in the specification, it is intended that the specification also provides a description of the components, parts, portions, of such apparatus.

Although the dependent claims have single dependencies in accordance with U.S. patent practice, each of the features in any of the dependent claims can be combined with each of the features of other dependent claims or the main claim.

It should be understood that various changes and modifications to the presently preferred embodiments described herein will be apparent to those skilled in the art. Such change and modifications can be made without departing from the spirit and scope of the present subject matter and without diminishing its intended advantages. It is therefore intended that such changes and modifications be covered by the appended claims.

We claim:

1. A system for measuring one or more physiological properties of a biological sample, the system comprising:

a well plate having a plurality of wells, the wells having an open end and a closed end opposite the open end;

an apparatus comprising:

a lid having a first surface and a second surface;

a plurality of spines connected to and extending from the first surface of the lid, each of the plurality of spines comprising a body having a distal end wherein at least one spine of the plurality of spines comprises one or more sensors, and wherein the lid forms a continuous surface once connected to the plurality of spines;

wherein the plurality of spines extend into the wells through the open end to a pre-determined depth within the well when the lid is positioned on the well plate;

wherein the distal end of the spines are spaced-apart from a respective well bottom of the well plate to form a sub-chamber within the well;

wherein the one or more sensors are disposed on at least one spine of the plurality of spines, wherein the one or more sensors engage and provide a signal responsive to a gradient of one or more analytes that are formed from the biological sample consuming or producing the one or more analytes;

wherein the lid has a coupling for allowing movement of the lid from a first position to one or more second positions with respect to the well; and a processor in communication with the coupling to provide automated motion of the lid so as to move the lid from the first position to a second position, thereby modifying the depth of the distal end of the spine into its respective well;

the one or more sensors coupled to a signal processor, the signal processor configured to:

interrogate the one or more sensors to obtain readings at the first position and second position; and compute a change in concentration in the gradient from the readings.

2. The system of claim 1, wherein at least one of the at least sensors is a fluorescent indicator.

3. The system of claim 1, wherein at least one of the at least twe sensors is an indicator embedded in a permeable medium.

4. The system of claim 1, wherein at least one of the at least twe sensors is a capture reagent.

5. The system of claim 1, wherein each of the plurality of spines has a length, and the length is between 1 mm and 20 mm.

6. The system of claim 5, wherein the plurality of spines collectively has a mean length, and the length of each of the plurality of spines is within 20% of the mean length.

7. The system of claim 1, wherein each of the plurality of spines comprises an impeller on the body.

8. The system of claim 1, wherein the plurality of spines extend into the wells, wherein the distal end of each of the plurality of spines is between 50 micrometers and 800 micrometers from the closed end of the well.

9. The system of claim 1, further comprising a signal detector in a position to detect a signal from the one or more sensors.

10. The system of claim 9, wherein at least one of the sensors is positioned on an opposite side of the closed end of the well plate from the signal detector.

11. The system of claim 1, wherein the coupling comprises a handle attached to the lid.

12. The system of claim 1, wherein each of the plurality of spines is solid.

13. A method for measuring one or more physiological properties of a biological sample, the method comprising:

providing a lid having a first surface and a second surface and a plurality of spines connected to and extending from the first surface of the lid, each of the plurality of spines comprising a body having a distal end, and wherein the lid forms a continuous surface once connected to the plurality of spines; and applying one or more sensors to the distal end of at least one of the plurality of spines, wherein the one or more sensors engage and provide a signal responsive to one or more analytes that are formed from the biological sample consuming or producing the one or more analytes;

positioning the lid on a well plate having a plurality of wells, the wells having an open end and a closed end opposite the open end;

wherein the plurality of spines extend into the wells through the open end to a pre-determined depth within the well when the lid is positioned on the well plate;

wherein the distal end of the spines are spaced-apart from a respective well bottom for the well plate to form a sub-chamber within the well;

wherein the lid has a coupling for allowing controlled movement of the lid via a processor in communication with the coupling;

controlling motion of the lid from a first position to one or more second positions with respect to the well, thereby modifying the depth of the distal end of the spine into its respective well;

interrogating the one or more sensors to obtain readings at the first position and second position; and computing a change in concentration in the gradient from the readings.

14. The method of claim 13, wherein the one or more sensors are applied as a mixture of a fluorescent indicator in a medium, and the one or more sensors are attached to the plurality of spines by solidifying or removing the medium.

15. The method of claim 13, wherein the one or more sensors are applied by dipping or spotting the distal end of at least one of the plurality of spines in a mixture of a fluorescent indicator in a medium.

16. The method of claim 13, wherein the lid is provided by molding a polymer material to form the lid and the plurality of spines.

17. The method of claim 13, wherein the coupling comprises a handle attached to the lid.

18. The method of claim 13, wherein each of the plurality of spines is solid.

19. A system for measuring one or more physiological properties of a biological sample, the system comprising:

a well plate having a plurality of wells, the wells having an open end and a closed end opposite the open end;

an apparatus comprising:

a lid having a first surface and a second surface;

a plurality of spines connected to and extending from the first surface of the lid, each of the plurality of spines comprising a body having a distal end wherein at least one spine of the plurality of spines comprises one or more sensors, each of the spines being solid such that the spines do not include cavities or hollow regions;

wherein the plurality of spines extend into the wells through the open end to a pre-determined depth within the well when the lid is positioned on the well plate;

wherein the distal end of the spines are spaced-apart from a respective well bottom of the well plate to form a sub-chamber within the well;

wherein the one or more sensors are disposed on at least one spine of the plurality of spines, wherein the one or more sensors engage and provide a signal responsive to a gradient of one or more analytes that are formed from a biological sample consuming or producing the one or more analytes;

wherein the lid has a coupling for allowing movement of the lid from a first position to one or more second positions with respect to the well; and a processor in communication with the coupling to provide automated motion of the lid so as to move the lid from the first position to a second position, thereby modifying the depth of the distal end of the spine into its respective well;

the one or more sensors coupled to a signal processor, the signal processor configured to:

interrogate the one or more sensors to obtain readings at the first position and second position; and compute a change in concentration in the gradient from the readings.

* * * * *